United States Patent
Tanner et al.

(10) Patent No.: US 10,426,455 B2
(45) Date of Patent: Oct. 1, 2019

(54) SURGICAL ANCHOR AND METHOD OF USE

(71) Applicant: Westek, LLC, Fresno, CA (US)

(72) Inventors: Cary Tanner, Fresno, CA (US); Toby R. Johnson, Fresno, CA (US)

(73) Assignee: Westek, LLC, Fresno, CA (US)

( * ) Notice: Subject to any disclaimer, the term of this patent is extended or adjusted under 35 U.S.C. 154(b) by 744 days.

(21) Appl. No.: 15/015,549

(22) Filed: Feb. 4, 2016

(65) Prior Publication Data

US 2017/0224327 A1 Aug. 10, 2017

(51) Int. Cl.
*A61B 17/04* (2006.01)
*A61B 17/06* (2006.01)

(52) U.S. Cl.
CPC .... *A61B 17/0401* (2013.01); *A61B 17/06166* (2013.01); *A61B 17/06066* (2013.01); *A61B 2017/044* (2013.01); *A61B 2017/0417* (2013.01); *A61B 2017/061* (2013.01); *A61B 2017/06176* (2013.01)

(58) Field of Classification Search
CPC ............ A61B 17/0401; A61B 17/7032; A61B 17/0642; A61B 2017/0414; A61B 2017/0417; A61B 2017/0459; A61B 2017/0409; A61F 2/0811; A61F 2002/0852; A61F 2002/0882; A61F 2002/0817; A61F 2002/0858; A61F 2002/0876

See application file for complete search history.

(56) References Cited

U.S. PATENT DOCUMENTS

| | | | |
|---|---|---|---|
| 7,163,540 B2 | 1/2007 | Martello | |
| 2005/0059972 A1 | 3/2005 | Biscup | |
| 2007/0198018 A1 | 8/2007 | Biedermann et al. | |
| 2007/0219557 A1* | 9/2007 | Bourque | A61B 17/0401 606/326 |
| 2008/0125815 A1* | 5/2008 | Heaven | A61B 17/0401 606/308 |
| 2008/0132956 A1 | 6/2008 | Biedermann et al. | |
| 2008/0132957 A1 | 6/2008 | Matthis et al. | |
| 2010/0057141 A1 | 3/2010 | Abdelgany et al. | |
| 2011/0066185 A1* | 3/2011 | Wotton, III | A61B 17/0401 606/228 |
| 2012/0123416 A1* | 5/2012 | Gelfand | A61B 17/0401 606/79 |
| 2014/0031791 A1 | 1/2014 | Russell et al. | |

FOREIGN PATENT DOCUMENTS

WO WO2017136180 A1 8/2017

OTHER PUBLICATIONS

"International Search Report" and "Written Opinion of the International Searching Authority," Patent Cooperation Treaty Application No. PCT/US2017/14618, dated May 26, 2016, 12 pages.
"International Search Report" and "Written Opinion of the International Searching Authority," Patent Cooperation Treaty Application No. PCT/US2017/014618, dated May 26, 2016, 12 pages.

* cited by examiner

Primary Examiner — Diane D Yabut
(74) Attorney, Agent, or Firm — Carr & Ferrell LLP

(57) ABSTRACT

A surgical anchor and methods of use are disclosed. A variety of surgical techniques may be practiced to repair torn connections between soft tissue, such as tendons and ligaments, and bone. The surgical anchor simplifies the surgical techniques by channeling repair sutures from the soft tissue through a bore in the surgical anchor and then immobilizing the repair sutures between the surgical anchor and the bone.

8 Claims, 20 Drawing Sheets

SURGICAL ANCHOR AND METHOD OF USE

FIELD OF THE INVENTION

The present technology relates generally to medical devices, and, more particularly, to a surgical anchor and method of use.

BACKGROUND OF THE DISCLOSURE

The human body contains a wide variety of soft tissue connections to bone, comprising primarily tendons connecting muscles to bones and ligaments connecting bones to other bones. Excessive strain can tear or even completely sever the connection between the soft tissue and bone. In many situations, a surgical procedure may be required to reattach the soft tissue to the bone. For example, a common surgical procedure is reattachment of the distal biceps tendon to the radius.

SUMMARY

The present disclosure may be directed to surgical anchors. An exemplary surgical anchor may comprise a shaft having a side wall, a top end, a terminal end, and a central axis extending from the top end to the terminal end. A head may be positioned at the top end of the shaft, the head comprising a beveled bottom surface oriented at a first angle relative to the central axis of the shaft. A central bore may extend through at least a portion of the shaft along the central axis. A first side bore may extend from the shaft side wall to the central bore and may be angled at a second angle relative to the central axis of the shaft. The first side bore may comprise a first opening in the shaft side wall positioned proximate to an intersection of the bottom surface of the head and the shaft side wall. A second side bore may be positioned a radial distance around the shaft from the first bore, the second side bore extending from the shaft side wall to the central bore. The second side bore may be angled at a third angle relative to the central axis of the shaft, and may comprise a second opening in the shaft side wall positioned proximate to the intersection of the bottom surface of the head and the shaft side wall.

According to additional exemplary embodiments, the present disclosure may be directed to a method for using a surgical anchor. An exemplary method may comprise selecting a surgical anchor. The surgical anchor may comprise a shaft having a side wall, a top end, a terminal end, and a central axis extending from the top end to the terminal end. A head may be positioned at the top end of the shaft, the head comprising a beveled bottom surface oriented at a first angle relative to the central axis of the shaft. A central bore may extend through at least a portion of the shaft along the central axis. A first side bore may extend from the shaft side wall to the central bore and may be angled at a second angle relative to the central axis of the shaft. The first side bore may comprise a first opening in the shaft side wall positioned proximate to an intersection of the bottom surface of the head and the shaft side wall. A second side bore may be positioned a radial distance around the shaft from the first bore, the second side bore extending from the shaft side wall to the central bore. The second side bore may be angled at a third angle relative to the central axis of the shaft, and may comprise a second opening in the shaft side wall positioned proximate to the intersection of the bottom surface of the head and the shaft side wall. A hole may be drilled through a bone and an edge of the hole may be chamfered. The hole may be adapted to receive the anchor. At least one suture may be captured and passed through the hole in the bone, through the central bore, and out one of the first or second side bores. The surgical anchor may be inserted into the hole in the bone, and secured into the hole such that the beveled bottom surface of the head contacts the chamfered edge of the hole, thereby immobilizing the at least one suture between the beveled bottom surface and the chamfered edge.

According to further exemplary embodiments, the present disclosure may be directed to a method for attaching tissue to bone. An exemplary method may comprise selecting a surgical anchor. The surgical anchor may comprise a shaft having a side wall, a top end, a terminal end, and a central axis extending from the top end to the terminal end. A head may be positioned at the top end of the shaft, the head comprising a beveled bottom surface oriented at a first angle relative to the central axis of the shaft. A central bore may extend through the shaft along the central axis. A first side bore may extend from the shaft side wall to the central bore and may be angled at a second angle relative to the central axis of the shaft. The first side bore may comprise a first opening in the shaft side wall positioned proximate to an intersection of the bottom surface of the head and the shaft side wall. A second side bore may be positioned a radial distance around the shaft from the first bore. The second side bore may extend from the shaft side wall to the central bore and may be angled at a third angle relative to the central axis of the shaft. The second side bore may comprise a second opening in the shaft side wall positioned proximate to the intersection of the bottom surface of the head and the shaft side wall. A hole may be drilled through a bone. An edge of the hole may be chamfered, and the hole may pass from a visible surgical field of view to a hidden surgical field of view. The hole may be adapted to receive the anchor. A tissue to be attached to the bone may be retrieved, and one or more sutures may be secured in the tissue. An elastomeric membrane may be placed adjacent to the hole in the hidden surgical field of view. A shuttle stitch comprising a leading end adapted to pass through the elastomeric membrane and a barb at the leading end may be selected. The barb may be adapted to resist movement of the shuttle stitch back through the elastomeric membrane, thereby capturing the shuttle stitch in the elastomeric membrane. The shuttle stitch may be inserted into the elastomeric membrane such that the barb passes into the elastomeric membrane. The elastomeric membrane and the captured shuttle stitch may be moved from the hidden surgical field of view to the visible surgical field of view. The shuttle stitch may be removed from the elastomeric membrane and coupled to the one or more sutures. The shuttle stitch and the coupled one or more sutures may be withdrawn back through the hole in the bone and then the shuttle stitch may be decoupled from the one or more sutures. The one or more sutures may be passed through the central bore of the surgical anchor and out one or both of the first and second side bores. The surgical anchor may be inserted into the hole in the bone. Excess slack in the one or more sutures may be removed such that the tissue is positioned against the bone. The surgical anchor may be secured in the hole in the bone such that the beveled bottom surface of the head contacts the chamfered edge of the hole, thereby immobilizing the one or more sutures between the beveled bottom surface and the chamfered edge.

According to still further exemplary embodiments, the present disclosure may be directed to a shuttle stitch. An exemplary shuttle stitch may comprise a stitch having a leading end, the leading adapted to pass through an elastomeric membrane. A barb may be positioned at the leading end. The barb may be adapted to resist movement of the stitch back through the elastomeric membrane.

According to yet additional exemplary embodiments, the present disclosure may be directed to a shuttle stitch kit. An exemplary shuttle stitch kit may comprise an elastomeric membrane and a shuttle stitch. The shuttle stitch may comprise a leading end adapted to pass through the elastomeric membrane and a barb at the leading end. The barb may be adapted to resist movement of the shuttle stitch back through the elastomeric membrane, thereby capture the shuttle stitch in the elastomeric membrane. The elastomeric membrane may be capable of transporting the captured shuttle stitch from a first position in a surgical field to a second position in the surgical field.

BRIEF DESCRIPTION OF THE DRAWINGS

The accompanying drawings, where like reference numerals refer to identical or functionally similar elements throughout the separate views, together with the detailed description below, are incorporated in and form part of the specification, and serve to further illustrate embodiments of concepts that include the claimed disclosure, and explain various principles and advantages of those embodiments.

The methods and devices disclosed herein have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION

Figure 1:
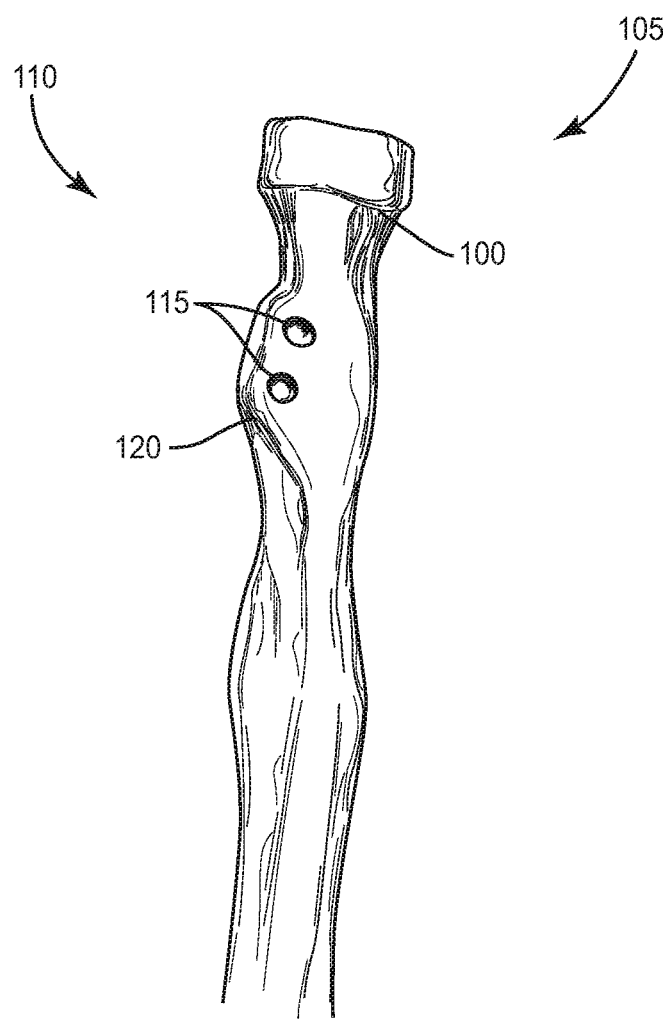
FIG. 1 is an anterior view of an upper extremity of a radius bone illustrating two holes placed in a radial tuberosity.

While this technology is susceptible of embodiment in many different forms, there is shown in the drawings and will herein be described in detail several specific embodiments with the understanding that the present disclosure is to be considered as an exemplification of the principles of the technology and is not intended to limit the technology to the embodiments illustrated.

The terminology used herein is for the purpose of describing particular embodiments only and is not intended to be limiting of the technology. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that like or analogous elements and/or components, referred to herein, may be identified throughout the drawings with like reference characters. It will be further understood that several of the figures are merely schematic representations of the present technology. As such, some of the components may have been distorted from their actual scale for pictorial clarity.

A variety of surgical techniques may be practiced to repair torn connections between soft tissue, such as tendons and ligaments, and bone. Particularly in the case of torn tendons, the repair procedure may involve drilling one or more holes in the bone to facilitate attachment of the tendon using sutures. The back side of the holes may be hidden from the surgical field of view, increasing the difficulty of the passing sutures through the holes. A typical prior art repair procedure for a torn distal biceps tendon is described below in reference to FIGS. 1 through 5.

FIG. 1 illustrates a proximal extremity of a radius 100 and a radial tuberosity 120 emanating from the radius 100 near the proximal end. Typically, an initial incision for the repair procedure is made on the anterior surface of the arm, exposing the anterior side of the radial tuberosity 120 to the visible surgical field of view 105. The distal biceps tendon (shown as 315 in FIG. 3) is reattached to the posterior side of the radial tuberosity 120, which is in the hidden surgical field of view 110 (that is, the posterior side of the radial tuberosity 120 is not directly visible to the surgeon through the incision). Two holes 115 may be drilled in the radial tuberosity 120 from the anterior side in the visible surgical field of view 105 through the posterior side in the hidden surgical field of view 110.

Figure 2:
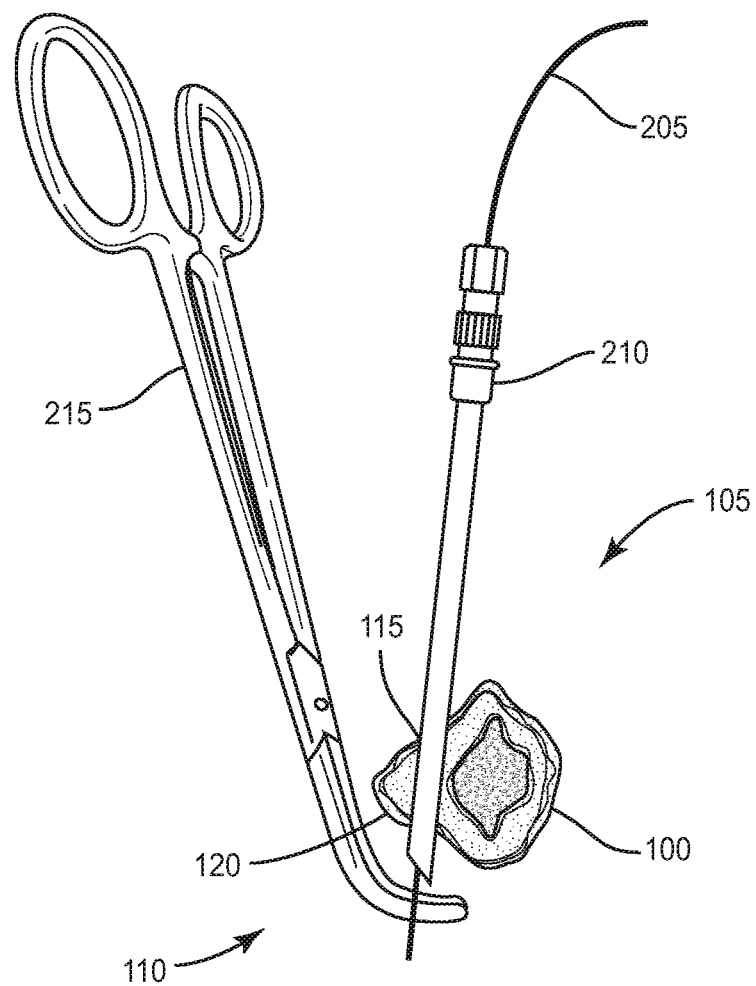
FIG. 2 is a top cross-sectional view of a radius bone illustrating a procedure for passing a shuttle stitch through a hole in a radial tuberosity.

FIG. 2 illustrates a surgical technique of using a hollow needle 210 (such as a spinal needle) to pass a shuttle stitch 205 (or suture) through one of the holes 115 in the radial tuberosity 120 from the visible surgical field of view 105 to the hidden surgical field of view 110 (that it, from the anterior side to the posterior side of the radial tuberosity 120). Since the end of the shuttle stitch 205 is now in the hidden surgical field of view 110, an instrument such as a right angle clamp 215 may be used to reach around to the posterior side of the radial tuberosity 120 and, by trial and error, grab the end of the shuttle stitch 205. This step of the procedure may require two surgeons, one to guide the hollow needle 210 and the shuttle stitch 205, and one to manipulate the right angle clamp to grab the end of the shuttle stitch 205. The process is then repeated for the second hole 115 in the radial tuberosity 120.

Figure 3:
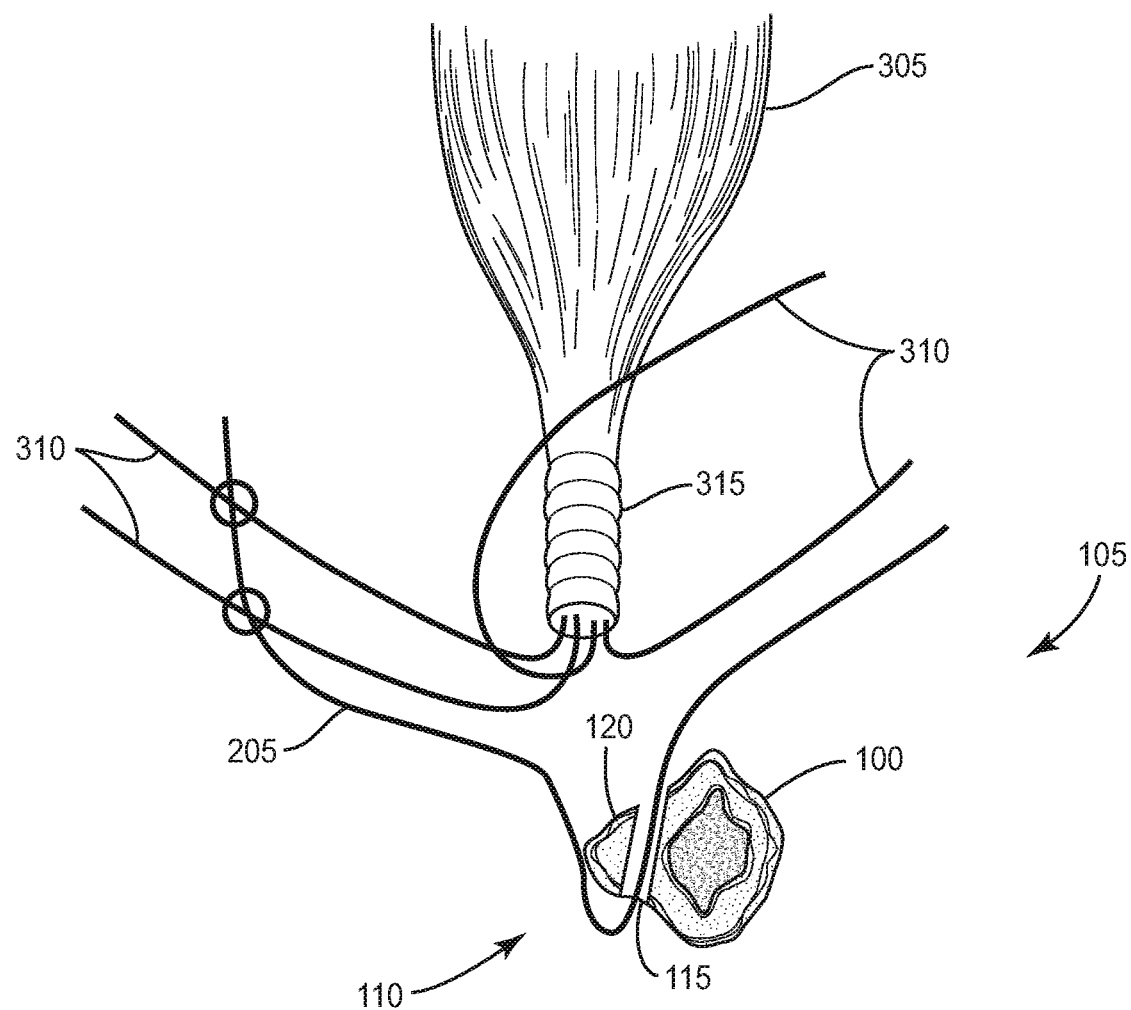
FIG. 3 is a top cross-sectional view of a radius bone and illustrating a biceps and biceps tendon with repair sutures coupled to a shuttle stitch.

In FIG. 3, the surgeon retrieves the retracted biceps tendon 315 of the biceps muscle 305 and secures at least two repair sutures 310 through the biceps tendon 315 such that all four ends of the at least two sutures 310 exit a distal end of the biceps tendon 315. In various embodiments, the two biceps tendon sutures 310 may comprise different materials and diameters. One of the shuttle stitches 205 may then be tied to one end of the first biceps tendon sutures 310 and one end of the second biceps tendon suture 310. The shuttle stitch 205 is then retracted back through the hole 115 in the radial tuberosity 120 from the posterior side to the anterior side and into the visible surgical field of view 105, which also retracts the ends of the first and second biceps tendon sutures 310 through the hole 115. The second shuttle stitch 205 may then be attached to the other ends of the first and second biceps tendon sutures 310 and retracted back through the hole 115 in the radial tuberosity 120 as was done with the first shuttle stitch 205.

Figure 4:
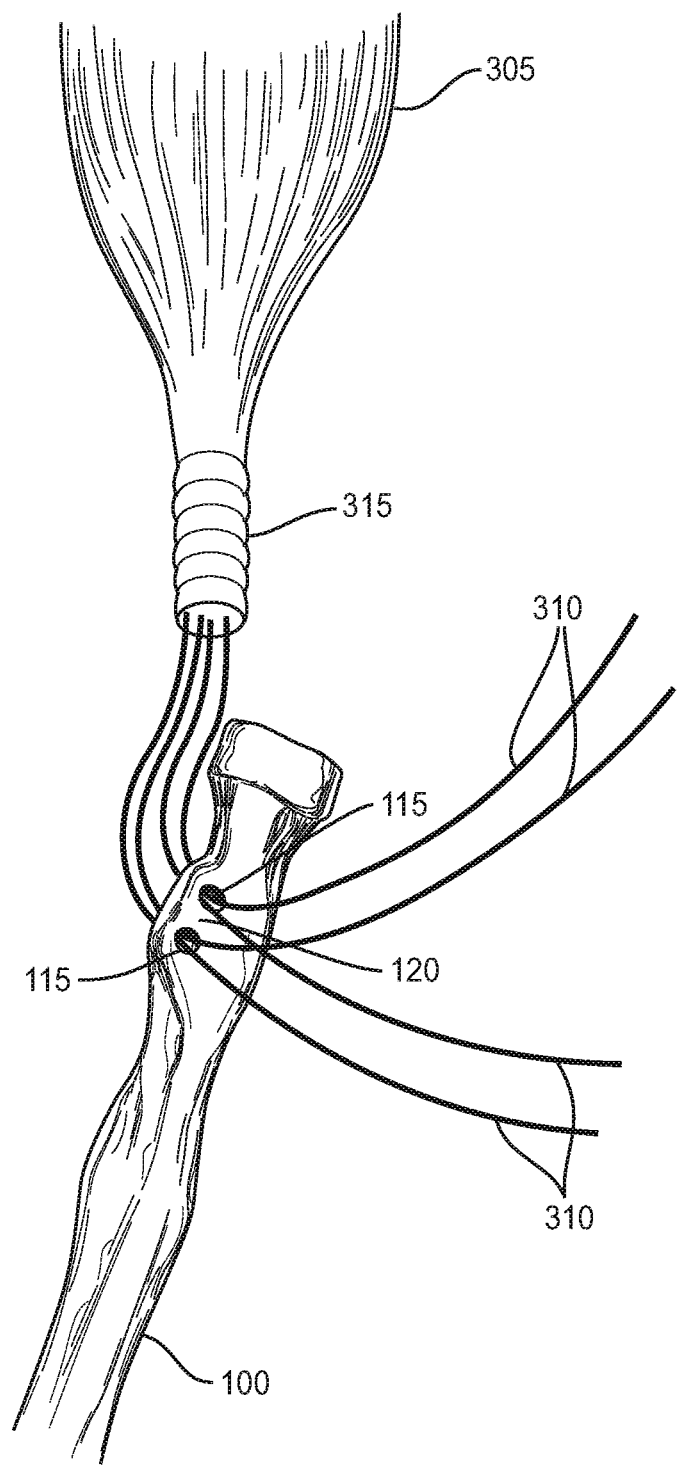
FIG. 4 is an anterior view of an upper extremity of a radius bone illustrating repair sutures in a biceps tendon pulled through holes in a radial tuberosity.
Figure 5:
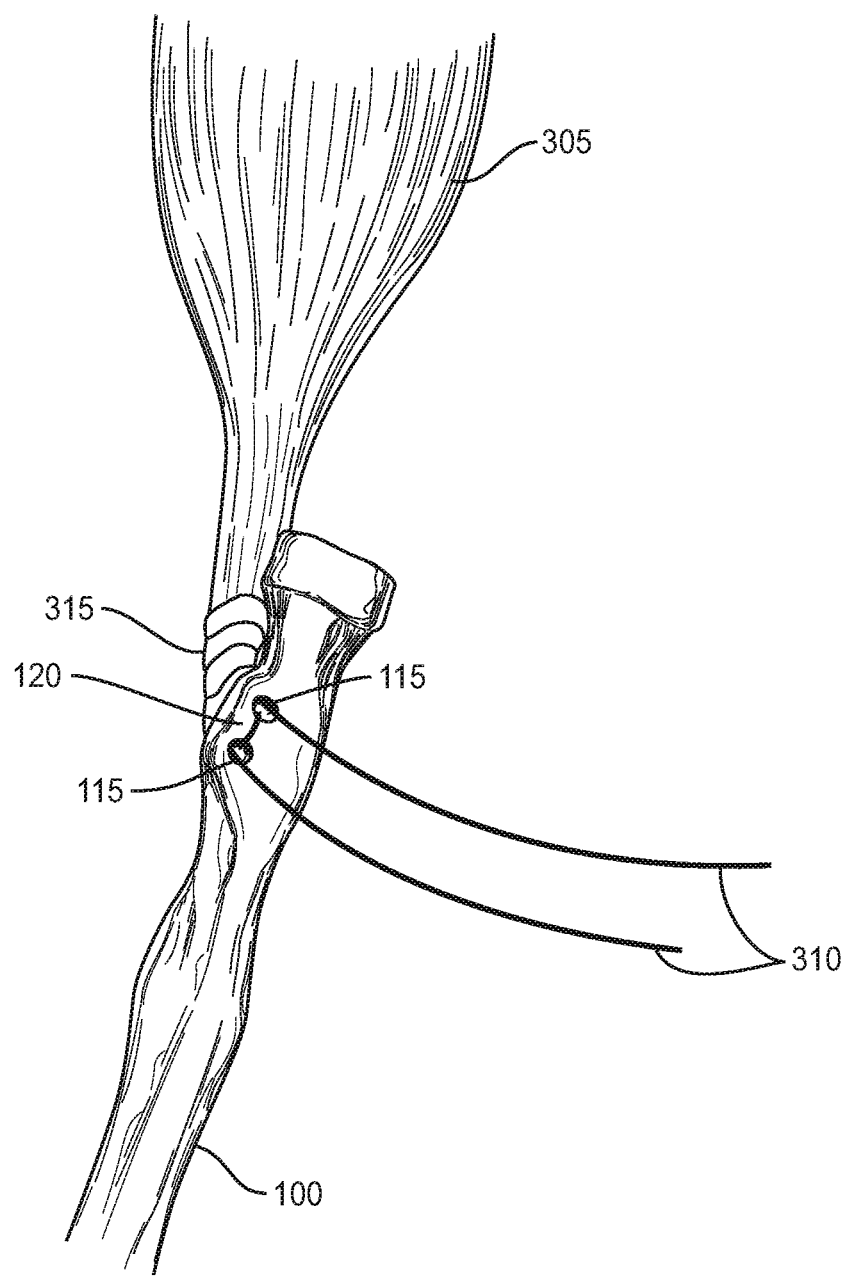
FIG. 5 is an anterior view of an upper extremity of a radius bone illustrating a biceps tendon anchored to a posterior side of a radial tuberosity using repair sutures.

Continuing to retract all four ends of the first and second biceps tendon sutures 310 through the holes 115 in the radial tuberosity 120 as illustrated in FIG. 4 pulls the biceps tendon 315 towards the posterior side of the radial tuberosity 120. Eventually, the biceps tendon 315 rests against the posterior side of the radial tuberosity 120 as illustrated in FIG. 5, and the four ends of the biceps tendon sutures 310 are tied off to hold the biceps tendon 315 in place.

The procedure described above in reference to FIGS. 1 through 5 suffers from a number of drawbacks. For example, the procedure generally requires two surgeons to transport the shuttle stitches 205 through the holes 115 in the radial tuberosity 120. This increases cost and ties up valuable resources. The procedure requires two holes 115 (as opposed to just one) to be drilled in the radial tuberosity 120, which increases the likelihood of infection and other complications in the bone. Additionally, the complicated transport of the shuttle stitches 205 and the drilling of multiple holes 115 increase the length of the surgery, which also increases costs and imposes heightened risk to the patient. An alternative procedure and surgical components as described below in reference to FIGS. 6 through 20 solves the problems associated with the previous procedure.

Figure 6:
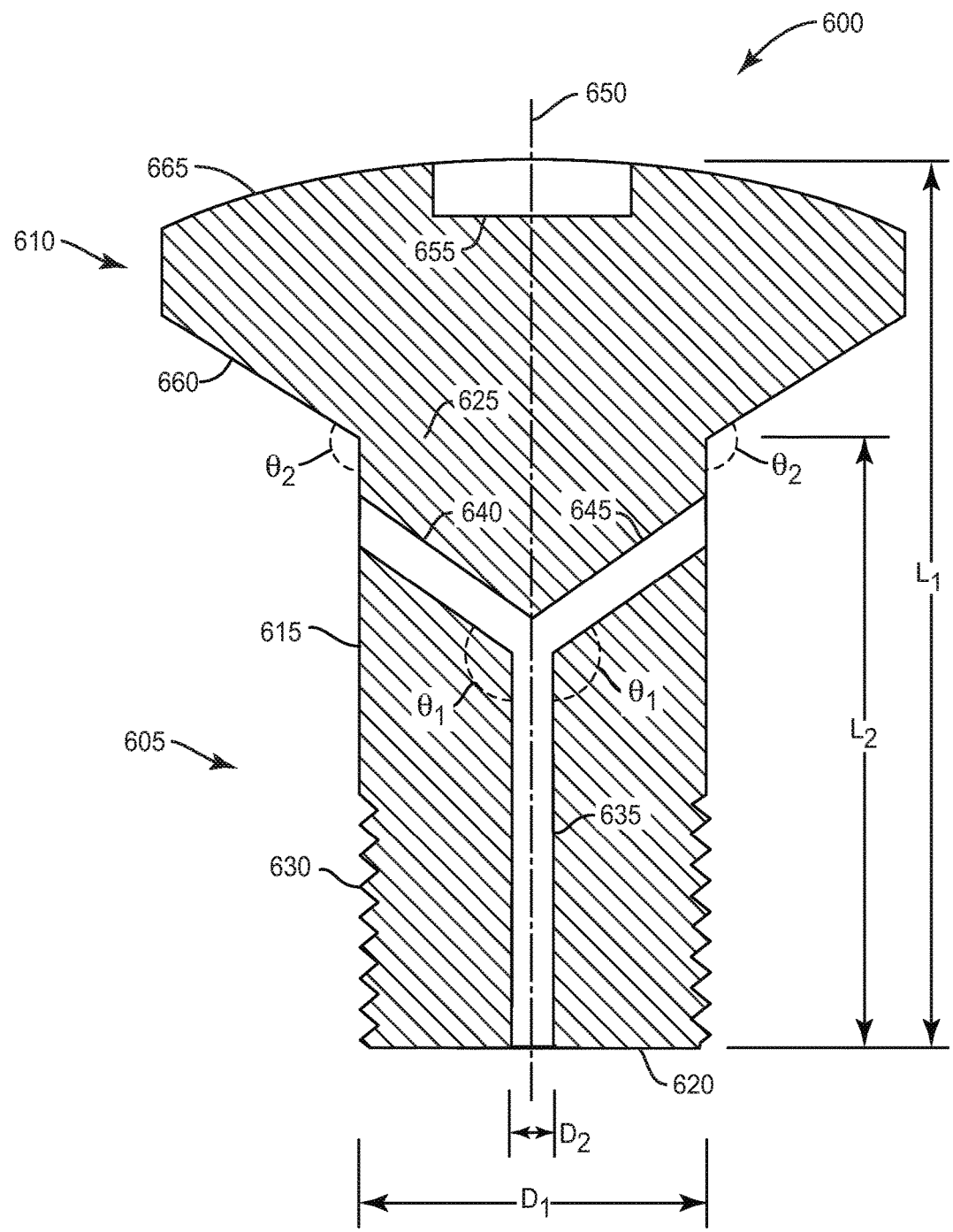
FIG. 6 is a front cross-sectional view of a surgical anchor according to various embodiments.

FIG. 6 illustrates various embodiments of a surgical anchor 600 for use in surgical procedures to attach or reattach tissue to bone. The surgical anchor 600 may comprise a shaft portion 605 and a head portion 610. The shaft 605 may further comprise a top end 625 and a terminal end 620, with a side wall 615 extending from the top end 625 to the terminal end 620. The head 610 may be circumferentially disposed about a central longitudinal axis 650 of the shaft 605. The head 610 may comprise a receptacle 655 for a driving tool (such as a screw driver, hex driver, star driver, etc.) in a top surface 665 of the head 610. A bottom surface 660 of the head 610 may be beveled at an angle $\theta_2$ with respect to the shaft central longitudinal axis 650, where the bevel angle $\theta_2$ may be greater than 90°. In various embodiments, the bevel angle $\theta_2$ may be equal to 90°.

A portion of the side wall 615 adjacent to the terminal end 620 may comprise threads 630 so that the surgical anchor 600 may be screwed into a bone (described in more detail below). In various embodiments, the shaft 605 may comprise any physical feature to promote coupling to a bone surface as is known in the art, such as protrusions (ridges, bumps, spikes, etc.) for a resistance fit. The surgical anchor 600 may also be coupled to the bone using an adhesive.

The shaft 605 may further comprise a central bore 635 beginning at the terminal end 620 and advancing along the central longitudinal axis 650 toward the top end 625 of the shaft 605. In various embodiments as illustrated in FIG. 6, the central bore 635 may terminate before reaching the top end 625. In other embodiments (not shown), the central bore 635 may continue further along the central axis 650, and in some embodiments may extend completely through the head 610. A first side bore 640 may originate on the side wall 615 of the shaft 605 in proximity to a point where the side wall 615 meets the bottom surface 660 of the head 610. The first side bore 640 may be angled downward towards the terminal end 620 of the shaft 605 at an angle $\theta_1$ with respect to the shaft central longitudinal axis 650. The angle $\theta_1$ may be greater than 90°, although the angle $\theta_1$ may be equal to 90° in various embodiments. In certain embodiments, the angle $\theta_1$ is equal to the angle $\theta_2$. In other embodiments, angles $\theta_1$ and $\theta_2$ are different. The first side bore 640 may proceed through the shaft 605 and terminate at the shaft central longitudinal axis 650 where it intersects the central bore 635 forming a continuous bore from the terminal end 620 of the shaft 605 to the side wall 615 of the shaft 605 in proximity to the intersection of the side wall 615 and the bottom surface 660 of the head 610.

A second side bore 645 may originate on the side wall 615 on an opposite side of the shaft 605 from the first side bore 640 (that is, the second bore 645 may be located 180° around the shaft 605 from the first bore 640). In various embodiments, the second side bore 645 is positioned a radial distance around the shaft 605 less than 180° from the first bore 640. The second side bore 645 may be angled downward towards the terminal end of 620 of the shaft 605 at an angle $\theta_1$ with respect to the shaft central longitudinal axis 650. The angle $\theta_1$ may be greater than 90°, although the angle $\theta_1$ may be equal to 90° in various embodiments. In certain embodiments, the angle $\theta_1$ is equal to the angle $\theta_2$. In other embodiments, $\theta_1$ and $\theta_2$ are different. The second side bore 645 may proceed through the shaft 605 and terminate at the shaft central longitudinal axis 650 where it intersects the central bore 635 forming a continuous bore from the terminal end 620 of the shaft 605 to the side wall 615 of the shaft 605 in proximity to the intersection of the side wall 615 and the bottom surface 660 of the head 610. Although FIG. 6 illustrates that the first and second side bores 640, 645 are oriented at the same angle $\theta_1$ with respect to the central longitudinal axis 650, there is no requirement that the angle $\theta_1$ be the same for the first and second side bores 640, 645. Any desired angle $\theta_1$ may be independently chosen for the first and second side bores 640, 645 as may be required for a particular indication.

Various embodiments may comprise a single side bore 640, or may comprise more side bores than the first and second side bores 640, 645.

The overall length $L_1$ of the surgical anchor 600 and the length $L_2$ of the shaft 605 may be selected as desired for the particular application. Shorter lengths $L_1$, $L_2$ may be chosen for small bones or thinner segments of bones, while longer lengths $L_1$, $L_2$ may be chosen for larger bones. The overall length $L_1$ of the surgical anchor 600 may range, for example, from about 30 mm to about 80 mm, although shorter and longer lengths $L_1$ are within the scope of the present disclosure. The shaft length $L_2$ may generally be a function of the specific head 610 shape and size chosen.

A diameter $D_1$ of the shaft 605 may vary from about 4.5 mm to about 6.5 mm, although larger and smaller diameters $D_1$ are within the scope of the present disclosure. A diameter $D_2$ of the central bore 635 may vary from about 0.05 mm to about 0.15 mm, depending on a diameter and count of the repair sutures 310 that will pass through the central bore 635 (as described below). A diameter of the first and second side bores 640, 645 may be the same as the diameter $D_2$ of the central bore 635, or may be different.

Figure 7:
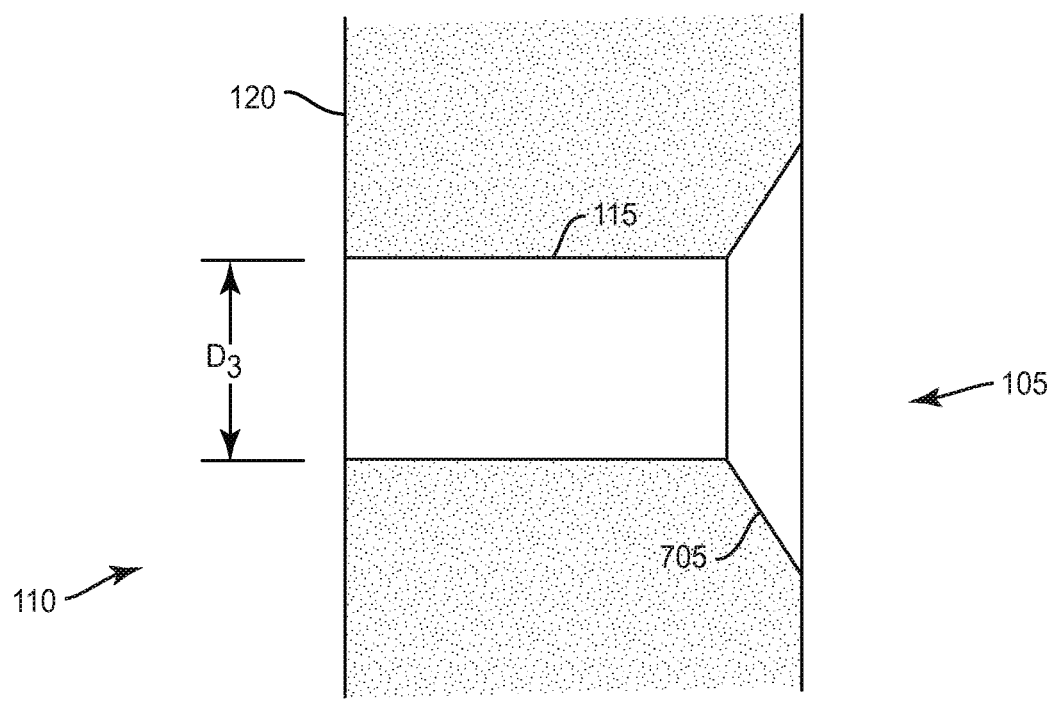
FIG. 7 is a front cross-sectional view of a bone with a chamfered hole according to various embodiments.

FIG. 7 is a schematic cross-sectional view of various embodiments of a bone, for example the radial tuberosity 120 described above, prepared for surgical attachment of a soft tissue such as the distal biceps tendon 315 to the radial tuberosity 120. The hole 115 may be drilled in the radial tuberosity 120 from the anterior side in the visible surgical field of view 105 through the posterior side in the hidden surgical field of view 110. An opening 705 of the hole 115 on the anterior side of the radial tuberosity 120 may be chamfered.

Figure 8:
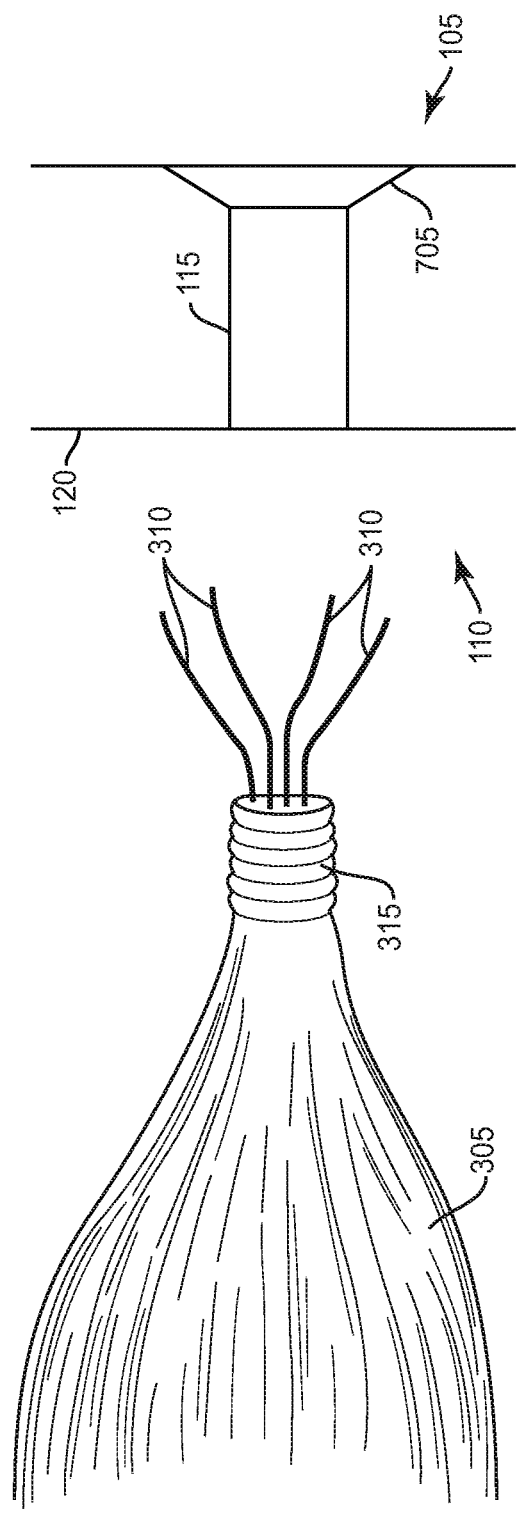
FIG. 8 is a front cross-sectional view of a bone with a chamfered hole and a tendon with repair sutures according to various embodiments.

In FIG. 8, the surgeon may retrieve the retracted biceps tendon 315 of the biceps muscle 305 and secure at least two repair sutures 310 through the biceps tendon 315 such that all four ends of the at least two sutures 310 exit a distal end of the biceps tendon 315. The biceps tendon 315 may be moved to the visible surgical field of view 105 for placement of the repair sutures 310. The sutured biceps tendon 315 may then be allowed to retract back to the hidden surgical field of view 110; however, the ends of the repair sutures 310 may remain in the visible surgical field of view 105 for later access.

Figure 9:
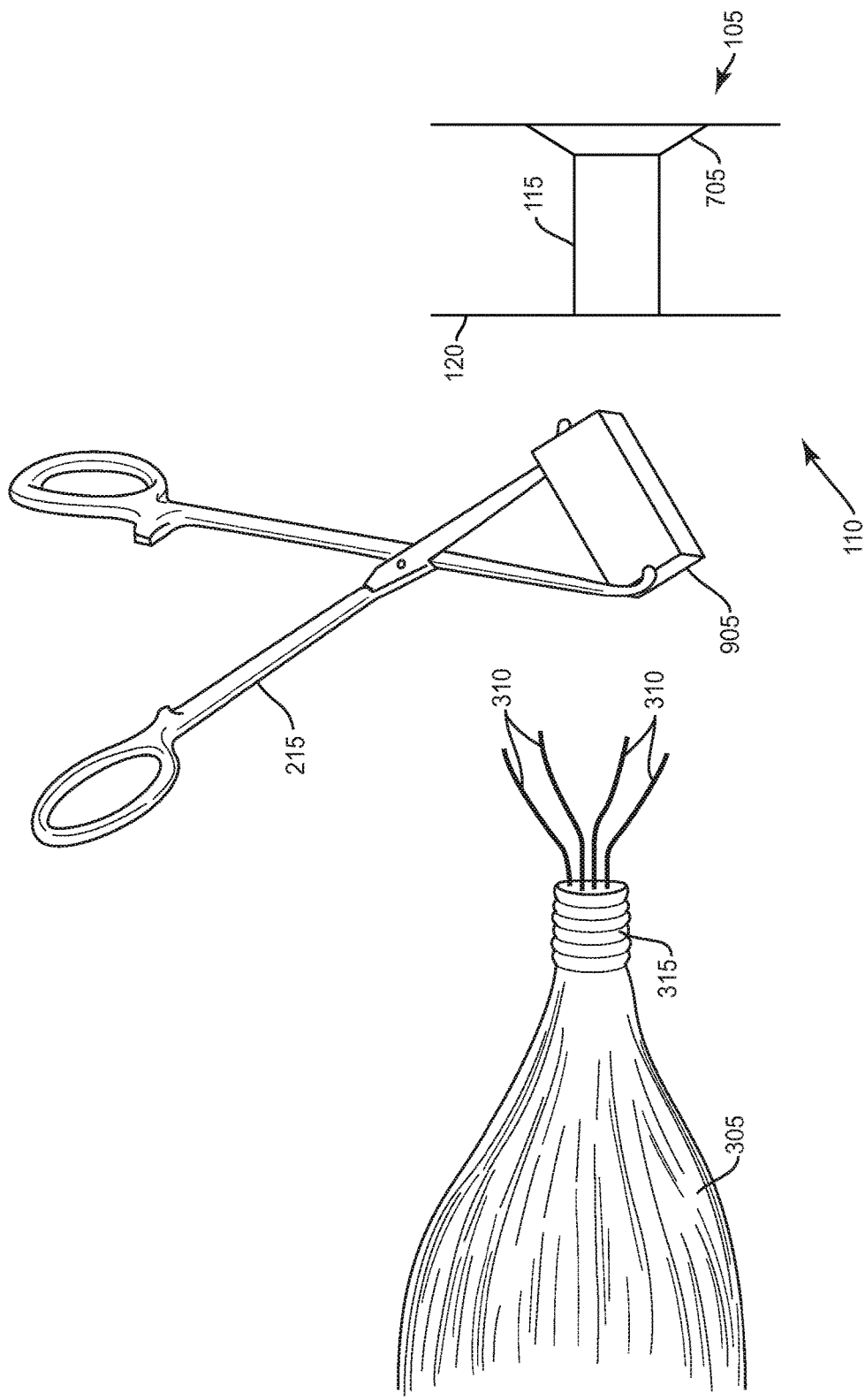
FIG. 9 is a front cross-sectional view of a bone with a chamfered hole and a tendon with repair sutures, illustrating placement of an elastomeric membrane on a posterior side of the bone according to various embodiments.

The surgeon may then select an elastomeric membrane 905 as illustrated in FIG. 9 according to various embodiments that is capable of being pierced by a sharp object. The elastomeric membrane 905 may have sufficient rigidity to be grasped by the right angle clamp 215 as shown in FIG. 9 without undue bending or folding. In certain embodiments, the elastomeric membrane 905 may comprise a handle (not shown) to eliminate the need for grasping the elastomeric membrane 905 with a clamp 215. By way of example, the elastomeric membrane 905 may comprise a saturated rubber such as ethylene propylene rubber, epichlorohydrin rubber, polyacrylic rubber, silicone rubber, fluorosilicone rubber, fluoroelastomer, perfluoroelastomers, polyether block amides, chlorosulfonated polyethylene, and ethylene-vinyl acetate. Further examples of the elastomeric membrane 905 may comprise unsaturated rubbers such as natural polyisoprene, synthetic polyisoprene, polybutadiene, chloroprene rubber, butyl rubber, halogenated butyl rubber, styrenebutadiene rubber, nitrile rubber, and hydrogenated nitrile rubber. Still further examples of the elastomeric membrane 905 may comprise thermoplastic elastomers, resilin, elastin, polysulfide rubber, and elastolefin.

In additional embodiments, the elastomeric membrane 905 may be flaccid (rather than rigid), such as a thin strip of elastomeric material. Rather than being held by inward pressure exerted by the clamp 215 as illustrated in FIG. 9, the flaccid elastomeric membrane 905 may be couple to the ends of the jaws of the clamp 215. The clamp 215 may remain closed, thereby maintaining a small profile for the elastomeric membrane 905 as it is inserted into place behind the radial tuberosity 120 as discussed below. The surgeon may the open the clamp 215 to expand the elastomeric membrane 905 so that it is rigid. Alternatively, an expandable forceps (not shown) may be used in place of the clamp 215. The elastomeric membrane 905 may be coupled to the ends of the jaws of the expandable forceps as described above for the clamp 215. The jaws of the expandable forceps may be in the closed position in order to insert the elastomeric membrane 905 into position, then the expandable forceps may be opened to expand the elastomeric membrane 905 so that it is rigid. As will be recognized by one skilled in the art, any suitable medical instrument may be used to hold and position the elastomeric membrane 905. The present disclosure and the accompanying figures should not be construed to be limiting to forceps-like devices.

Using the right angle clamp 215 (or the integral handle), the surgeon may then position the elastomeric membrane 905 behind the radial tuberosity 120 and in the hidden surgical field of view 110. The elastomeric membrane 905 may be placed directly behind the hole 115.

Figure 10:
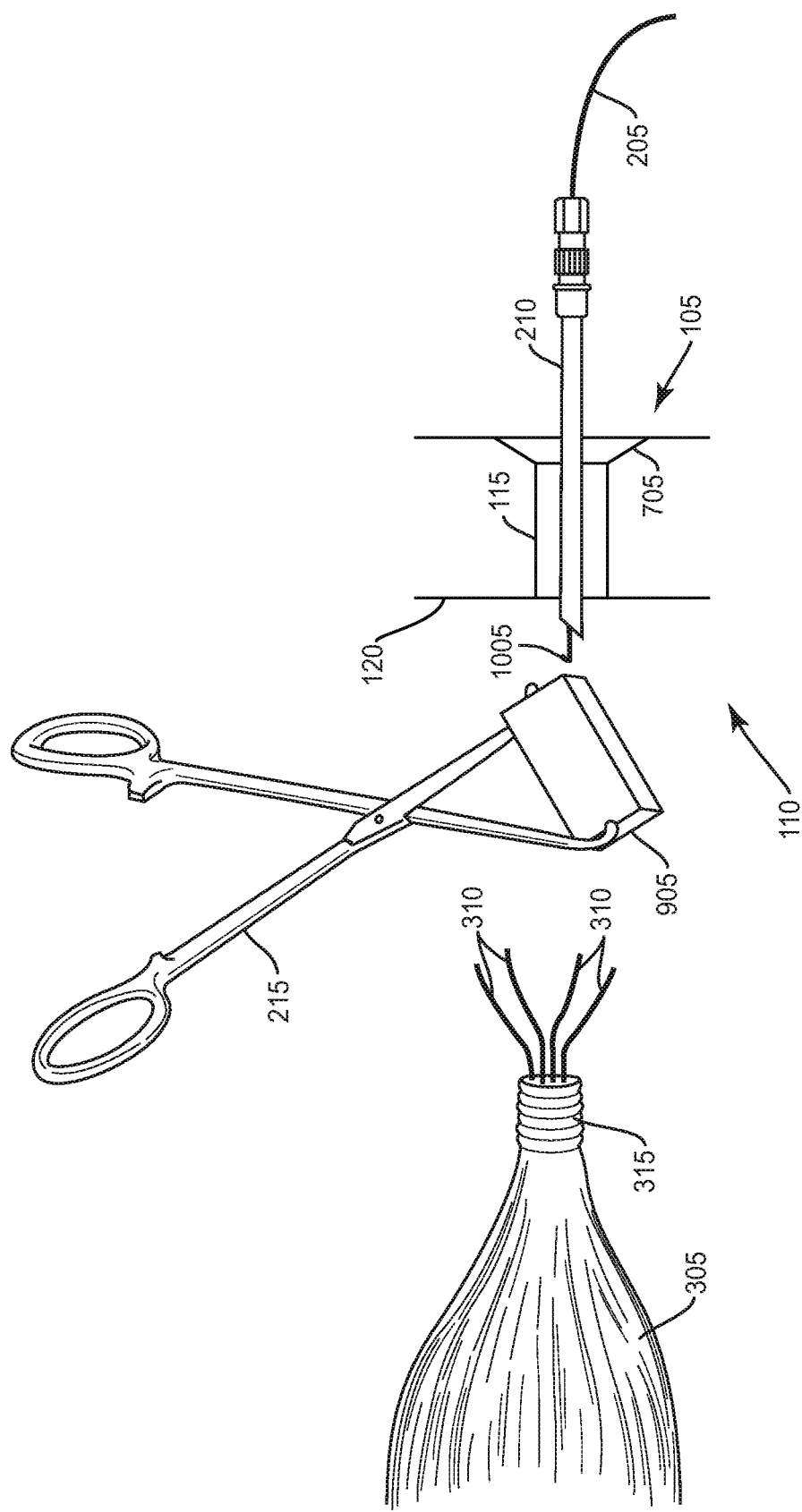
FIG. 10 is a front cross-sectional view of a bone with a chamfered hole and a tendon with repair sutures, illustrating passing a shuttle stitch through the hole according to various embodiments.

As illustrated in FIG. 10 according to various embodiments, a hollow needle 210 (such as a spinal needle) may be used to pass a shuttle stitch 205 (or suture) through the hole 115 in the radial tuberosity 120 from the visible surgical field of view 105 to the hidden surgical field of view 110 (that is, from the anterior side to the posterior side of the radial tuberosity 120). The shuttle stitch 205 may comprise a barb 1005 on a leading end. The barb 1005 may comprise any shape or functionality that will generally allow the barb 1005 to pass through a material in one direction and resist movement of the barb 1005 back through the material in the opposite direction. By way of example, the barb 1005 may comprise a hook formed in an end of the shuttle stitch 205, an L-shape formed from the leading end of the shuttle stitch 205, at least a portion of a circle formed from the leading edge of the shuttle stitch 205, or a helical shape formed form the leading edge of the shuttle stitch 205. In various embodiments, the barb 1005 may comprise a separate component coupled to the leading edge of the shuttle stitch 205.

In various embodiments, the barb 1005 may comprise an expanded or bulbous protrusion along a portion of a length of the shuttle stitch 205. The protrusion may be solidly formed into the length of the shuttle stitch 205, or may be formed by introducing a liquid or a gas into a hollow space within the shuttle stitch 205 such that pressure exerted by the liquid or gas causes a portion of the shuttle stitch 205 to expand to a larger diameter than an unexpanded portion of the shuttle stitch 205.

The surgeon may then advance the shuttle stitch 205 until the barb 1005 pierces the elastomeric membrane 905. The barb 1005 may be embedded within the elastomeric membrane 905, or may pass completely through the elastomeric membrane 905 as illustrated by various embodiments in FIG. 11.

In various embodiments, the hollow needle 210 may have a longitudinal bore for receiving the shuttle stitch 205. The barb 1005 may have a diameter greater than a diameter of the longitudinal bore such that the barb 1005 may not pass through the hollow needle 210. Thus, the hollow needle 210 itself may pierce the elastomeric membrane 905 and push the barb 1005 through the elastomeric membrane 905. The hollow needle 210 may then be retracted from the elastomeric membrane 905, leaving the barb 1005 in place in the elastomeric membrane 905.

Figure 11:
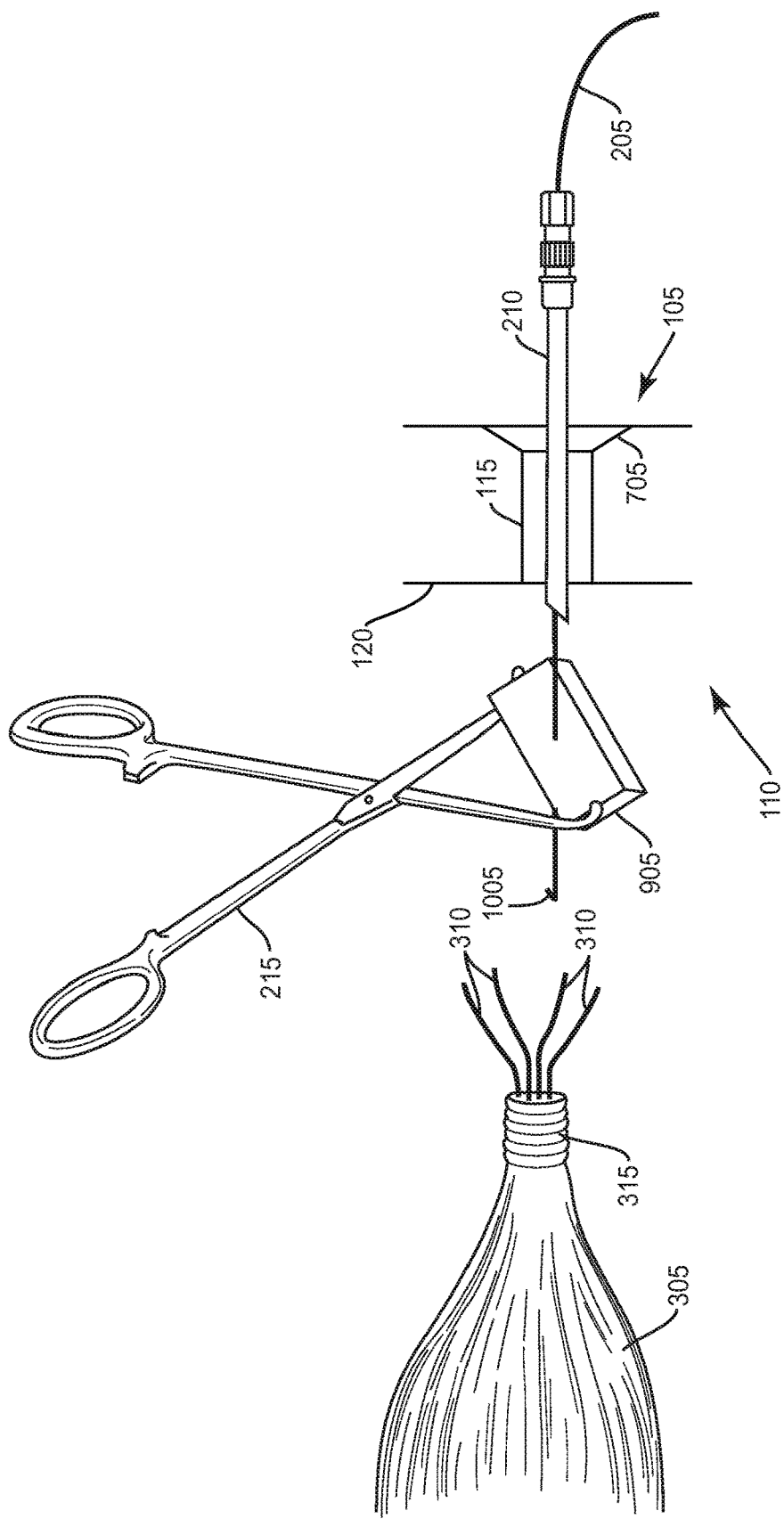
FIG. 11 is a front cross-sectional view of a bone with a chamfered hole and a tendon with repair sutures, illustrating inserting a shuttle stitch through an elastomeric membrane according to various embodiments.

In contrast to the procedure described above in reference to FIG. 2 where a second surgeon may be required to find and grasp an end of the shuttle stitch 205 with a clamp, the devices and methodology illustrated in FIGS. 10 and 11 may be carried out quickly and easily by a single surgeon. The use of the elastomeric membrane 905 allows the surgeon to place the elastomeric membrane 905 in the general vicinity of the hole 115 in the hidden surgical field of view 110 so that the elastomeric membrane 905 is in the path of the shuttle stich 205, which requires only gross positioning, not the precision positioning required as illustrated in FIG. 2. This eliminates the need for a second surgeon and reduces the length of the surgery, thereby saving valuable time and resources.

Figure 12:
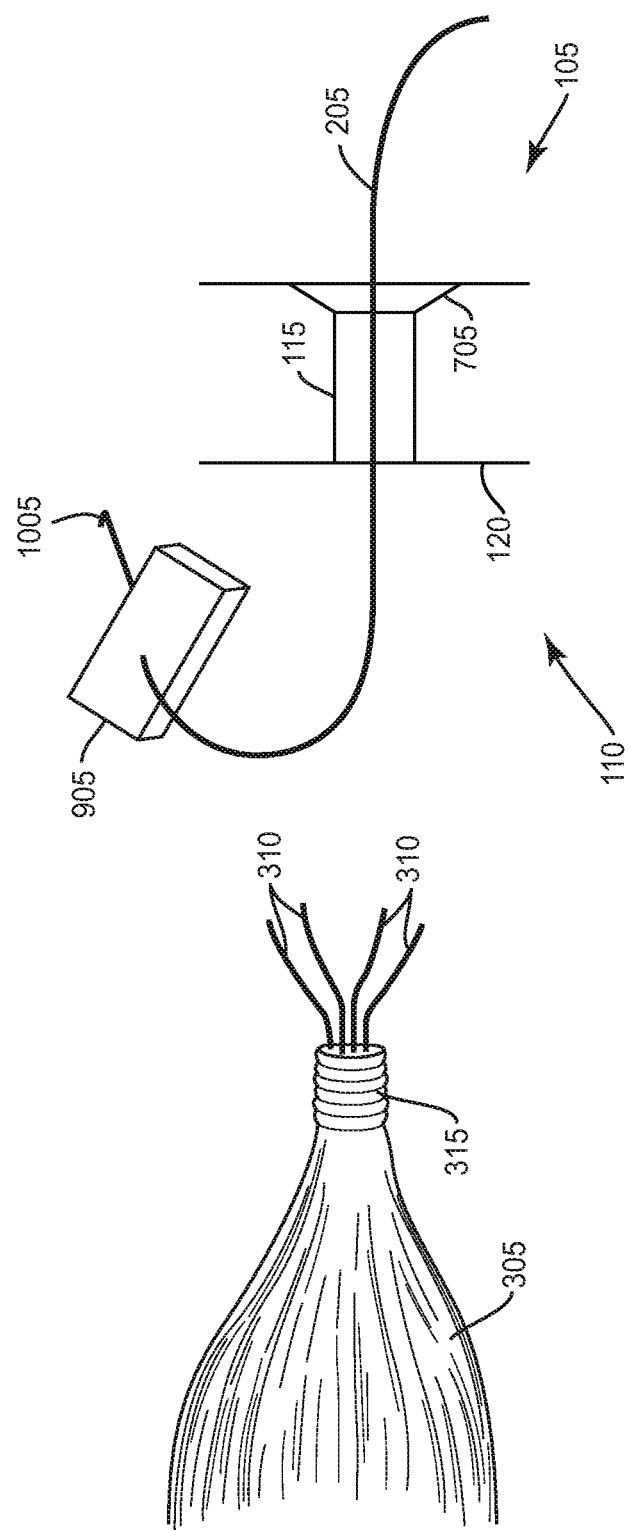
FIG. 12 is a front cross-sectional view of a bone with a chamfered hole and a tendon with repair sutures, illustrating using an elastomeric membrane to move a shuttle stitch from a hidden surgical field of view to a visible surgical field of view according to various embodiments.
Figure 13:
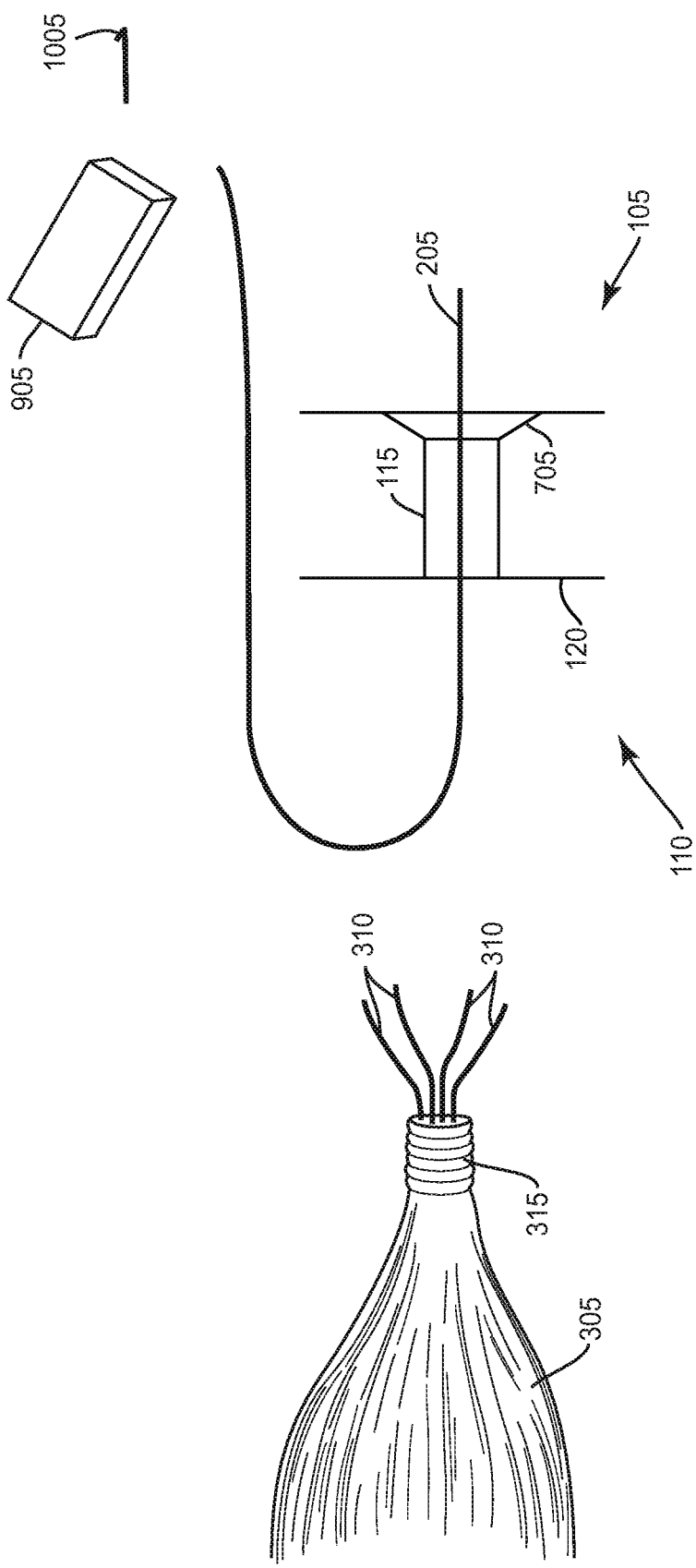
FIG. 13 is a front cross-sectional view of a bone with a chamfered hole and a tendon with repair sutures, illustrating removing a shuttle stitch from an elastomeric membrane in a visible surgical field of view according to various embodiments.

In FIG. 12, the surgeon moves the elastomeric membrane 905 into the visible surgical field of view 105 so that the leading end of the shuttle stitch 205 is now visibly accessible to the surgeon. The surgeon may then cut off the barb 1005 from the leading end of the shuttle stich 205 (FIG. 13) and may discard the barb 1005 and the elastomeric membrane 905.

Figure 14:
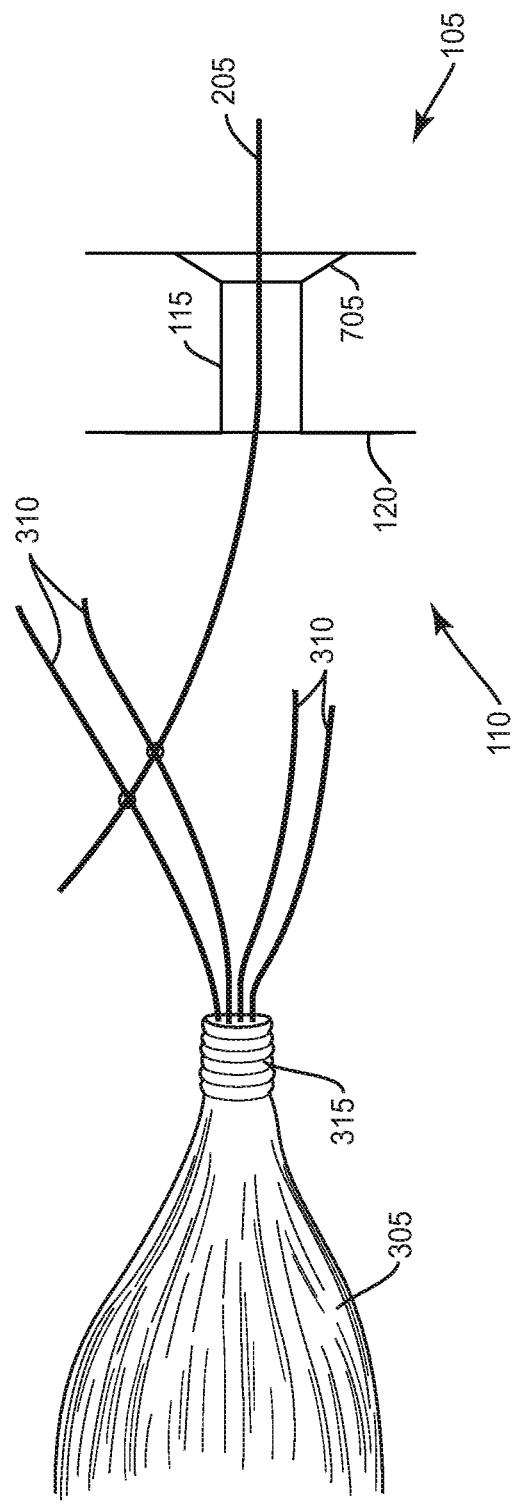
FIG. 14 is a front cross-sectional view of a bone with a chamfered hole and a tendon with repair sutures, illustrating coupling a shuttle stitch to the repair sutures according to various embodiments.
Figure 15:
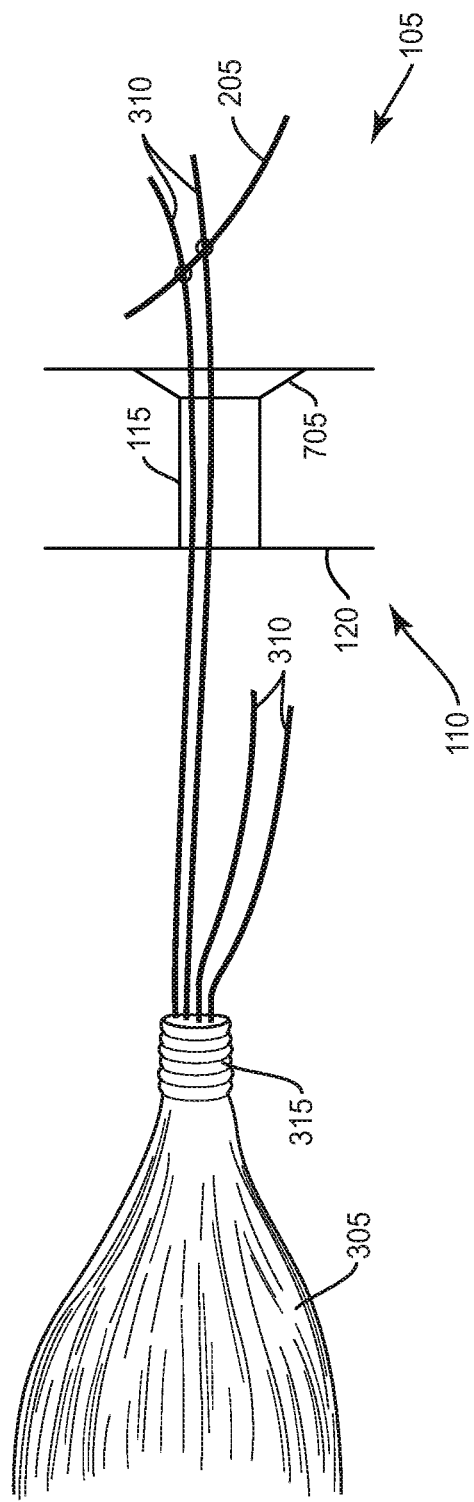
FIG. 15 is a front cross-sectional view of a bone with a chamfered hole and a tendon with repair sutures, illustrating using a shuttle stitch to pull the repair sutures through the hole according to various embodiments.

Next, the surgeon may couple the shuttle stitch 205 to one or more of the repair sutures 310 in the biceps tendon 315 as shown in FIG. 14. In FIG. 15, the surgeon may pull the shuttle stitch 205 and the coupled repair sutures 310 back through the hole 115 to the visible surgical field of view 105. The procedure illustrated in FIGS. 9 through 15 according to various embodiments may be repeated as necessary until all of the repair sutures 310 are brought through the hole 115 to the visible surgical field of view 105.

Figure 16:
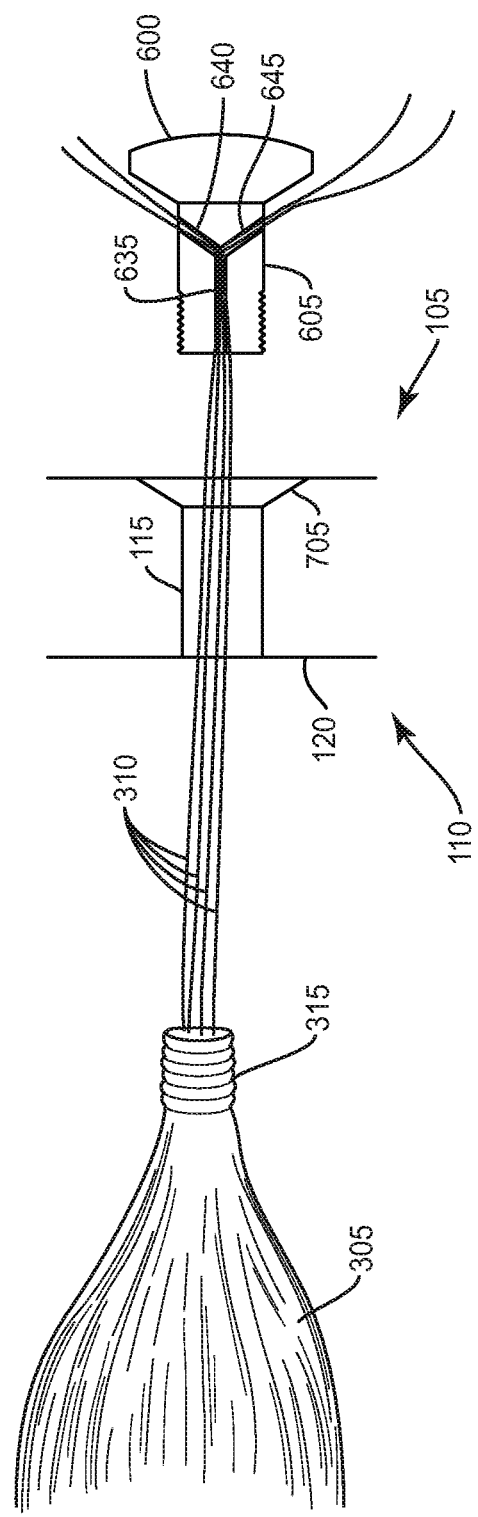
FIG. 16 is a front cross-sectional view of a bone with a chamfered hole and a tendon with repair sutures, illustrating passing the repair sutures through a bore in a surgical anchor according to various embodiments.
Figure 17:
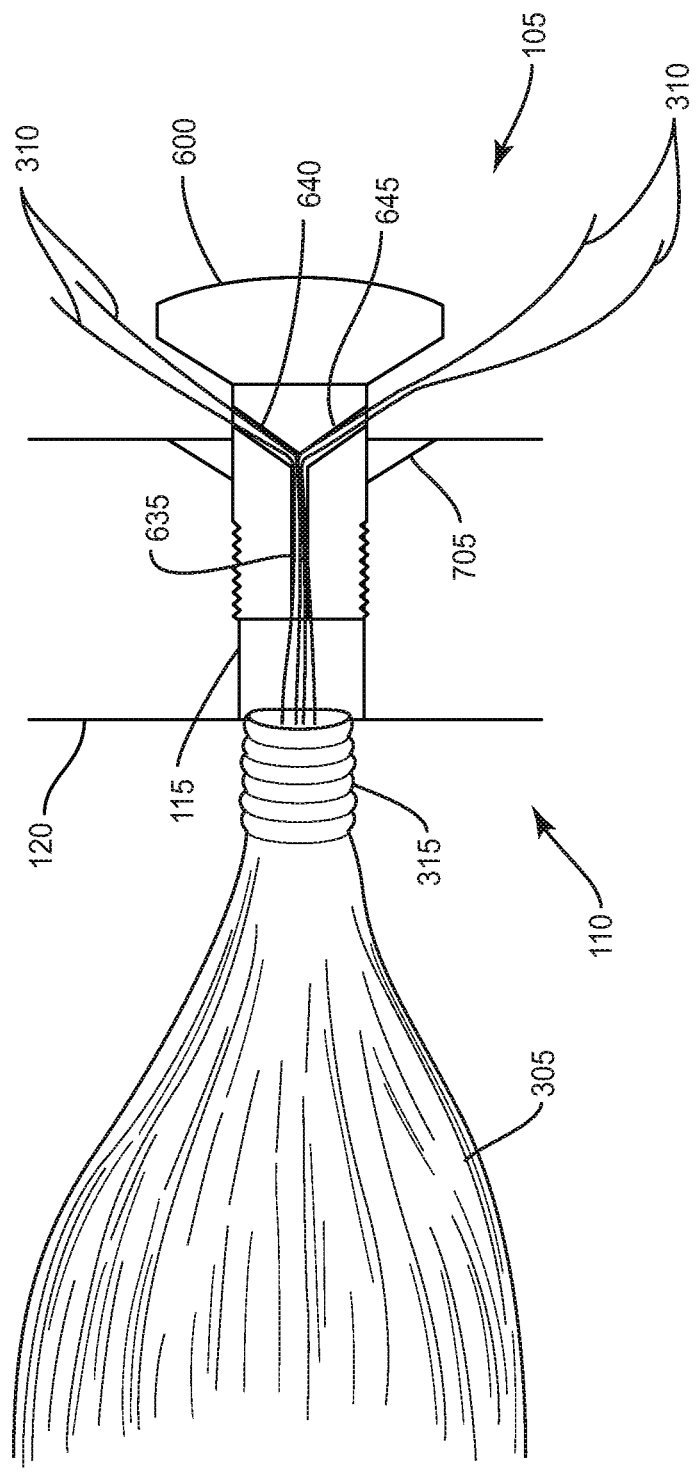
FIG. 17 is a front cross-sectional view of a bone with a chamfered hole and a tendon with repair sutures, illustrating a surgical anchor partially inserted into the hole with the repair sutures pulled through a bore in the surgical anchor to bring the tendon into contact with the bone according to various embodiments.

The repair sutures 310 may then be passed through the central bore 635 of the surgical anchor 600 and out one or more of the side bores 640, 645 as illustrated according to various embodiments in FIG. 16. The surgical anchor 600 may then be placed within the hole 115 in the radial tuberosity 120 until the side bores 640, 645 are slightly outside the chamfered edge 705 of the hole 115 as illustrated in FIG. 17 according to various embodiments. The surgeon may pull on the ends of the repair sutures 310 protruding from the side bores 640, 645 until the biceps tendon 315 is brought into contact with the posterior side of the radial tuberosity 120.

Figure 18:
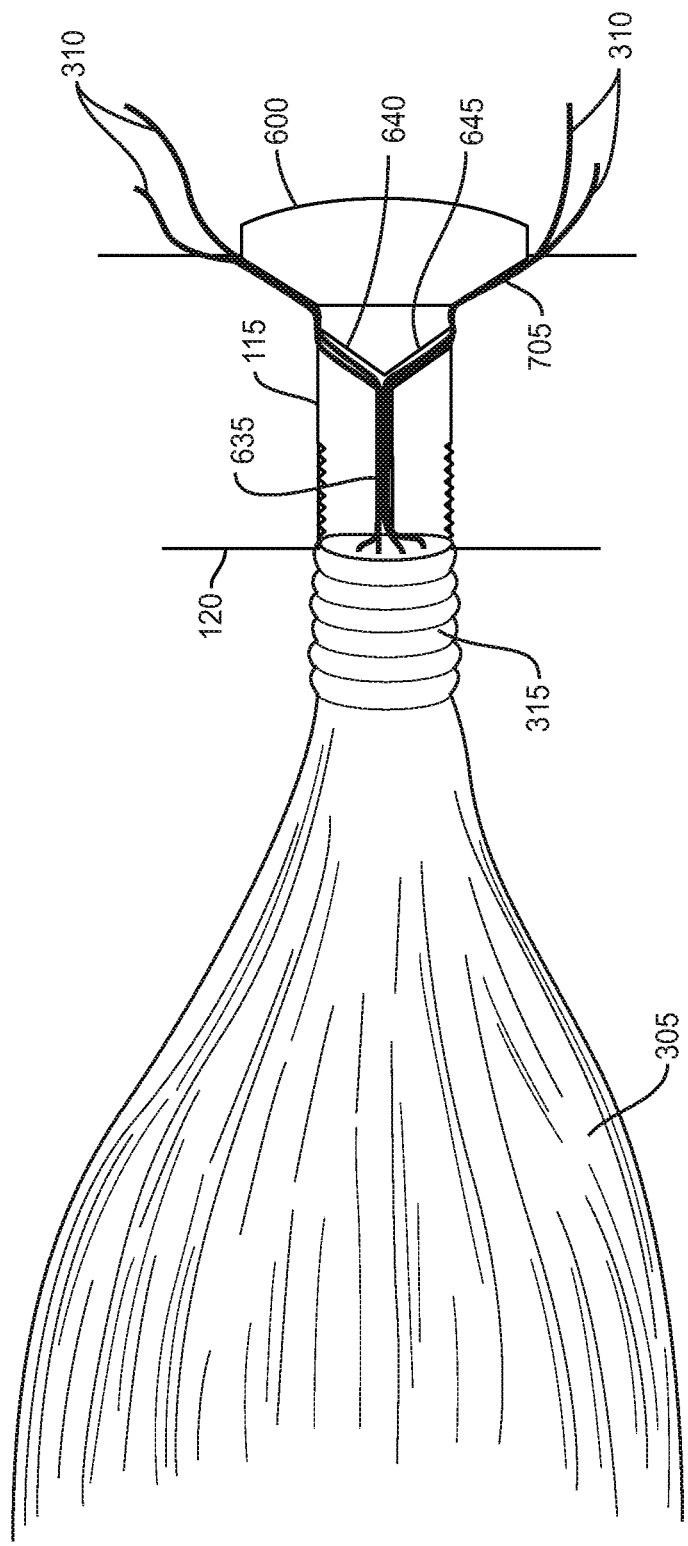
FIG. 18 is a front cross-sectional view of a bone with a chamfered hole and a tendon with repair sutures, illustrating a surgical anchor fully inserted into the hole and immobilizing the repair sutures to maintain contact between the tendon and the bone according to various embodiments.

As illustrated in FIG. 18 according to various embodiments, the surgeon may further insert the surgical anchor 600 into the hole 115 until the bottom beveled surface 660 of the surgical anchor 600 makes contact with the chamfered edge 705 of the hole 115, thereby trapping and generally immobilizing the repair sutures 310 therebetween. If desired, the loose ends of the repair sutures 310 may be tied off beside or on top of the surgical anchor 600.

Various embodiments may comprise a kit for a surgical procedure to facilitate a procedure similar to the procedure described above with respect to FIGS. 7 through 18 (or any portion thereof). The kit may comprise the elastomeric membrane 905 and the shuttle stitch 205. The shuttle stitch 205 may comprise a leading end adapted to pass through the elastomeric membrane 905, and a barb 1005 adapted to resist movement of the shuttle stitch 205 back through the elastomeric membrane 905 such that the shuttle stitch 205 may be captured in the elastomeric membrane 905. The elastomeric membrane 905 may be capable of transporting the captured shuttle stitch 205 from a first position in a surgical field to a second position in a surgical field.

The kit may further comprise the cannula 210 adapted to receive the shuttle stitch 205 therein and pass the shuttle stitch 205 through the elastomeric membrane 905. The cannula 210 may comprise a longitudinal axial bore having a first diameter to receive the shuttle stitch 205. The barb 1005 may have a second diameter greater than the first diameter of the longitudinal axial bore. In various embodiments, the kit may also comprise the clamp 215 (or forceps or other surgical device) to hold the elastomeric membrane 905 during the surgical procedure.

Although not shown, a sleeve may be placed within the hole 115 in the radial tuberosity 120. The sleeve may comprise a rigid material such as a metal or a polymer and may further comprise a threaded interior surface. The interior threaded surface may be adapted to receive the threaded portion 630 of the surgical anchor 600. Thus, the threaded portion 630 of the surgical anchor 600 may engage the sleeve rather than directly contacting bone in the hole 115.

Figure 19:
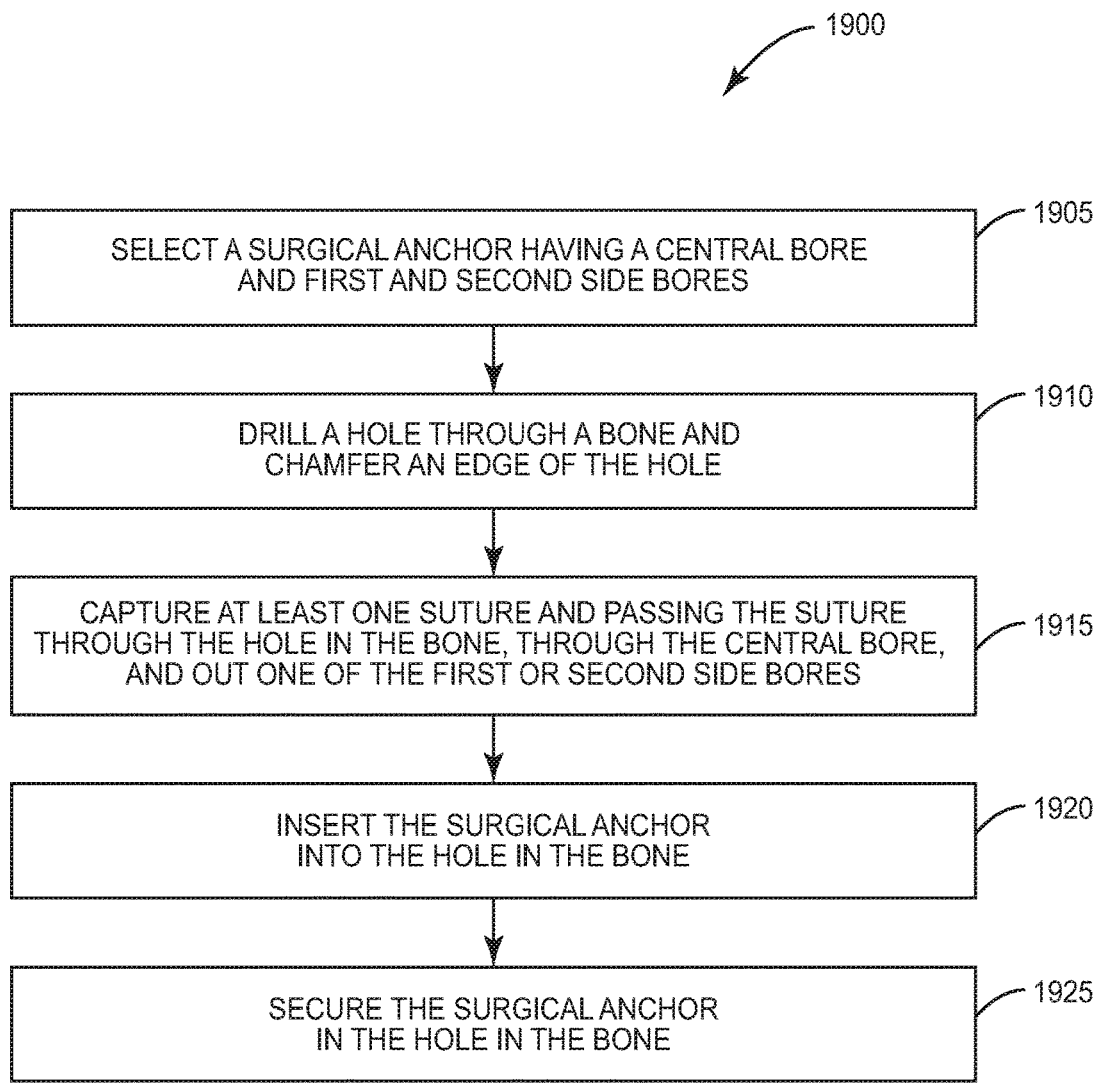
FIG. 19 is a flow diagram of an exemplary method for using a surgical anchor according to various embodiments.

FIG. 19 is a flowchart of an exemplary method 1900 for using a surgical anchor 600. At step 1905, a surgical anchor 600 may be selected. The surgical anchor may comprise a shaft 605 having a side wall 615, a top end 625, a terminal end 620, and a central axis 650 extending through the surgical anchor 600 from the top end 625 to the terminal end 620. The surgical anchor may further comprise a head 610 positioned at the top end 625 of the shaft 605, the head 610 may comprise a beveled bottom surface 660 oriented at a first angle $\theta_2$ relative to the central axis 650. A central bore 635 may extend through at least a portion of the shaft 605 along the central axis 650. The surgical anchor 600 may further comprise a first side shaft 640 and a second side shaft 645. The second side shaft 645 may be positioned a radial distance around the shaft 605 from the first side bore 640. Each of the first and second bores 640, 645 may be angled at a second angle $\theta_1$ relative to the central axis 650 of the shaft 605, and may comprise first and second openings, respectively, in the side wall 615 positioned proximate to an intersection of the bottom surface 660 of the head 610 and the side wall 615 of the shaft 605. At step 1910, a hole 115 may be drilled through a bone 100, and an edge 705 of the hole 115 may be chamfered. The hole 115 may be adapted to receive the surgical anchor 600. At least one suture 310 may be captured at step 1915 and passed through the hole 115 in the bone 100, through the central bore 635, and out one of the first or second side bores 640, 645. At step 1920, the surgical anchor 600 may be inserted into the hole 115 in the bone 100, and then secured in the hole 115 at step 1925.

Figure 20:
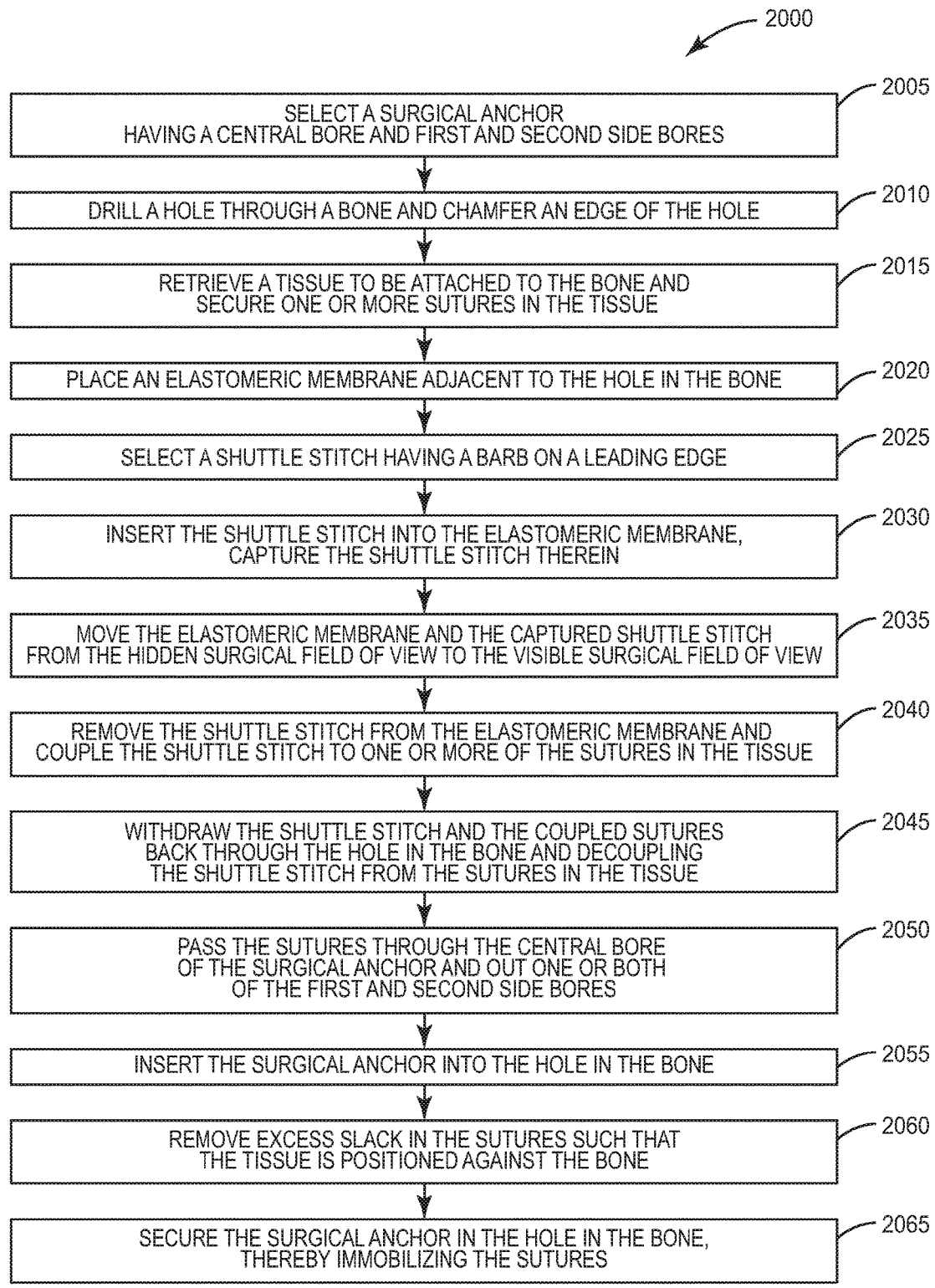
FIG. 20 is a flow diagram of an exemplary method for attaching tissue to bone according to various embodiments.

FIG. 20 is a flowchart of an exemplary method 2000 for attaching tissue to bone. At step 2005, a surgical anchor 600 may be selected. The surgical anchor 600 may comprise a shaft 605 having a side wall 615, a top end 625, a terminal end 620, and a central axis 650 extending through the surgical anchor 600 from the top end 625 to the terminal end 620. The surgical anchor may further comprise a head 610 positioned at the top end 625 of the shaft 605, the head 610 comprising a beveled bottom surface 660 oriented at a first angle $\theta_2$ relative to the central axis 650. A central bore 635 may extend through at least a portion of the shaft 605 along the central axis 650. The surgical anchor 600 may further comprise a first side shaft 640 and a second side shaft 645. The second side shaft 645 may be positioned a radial distance around the shaft 605 from the side first bore 640. Each of the first and second bores 640, 645 may be angled at a second angle $\theta_1$ relative to the central axis 650 of the shaft 605, and may comprise first and second openings, respectively, in the side wall 615 positioned proximate to an intersection of the bottom surface 660 of the head 610 and the side wall 615 of the shaft 605. At step 2010, a hole 115 may be drilled through a bone 100, and an edge 705 of the hole 115 may be chamfered. The hole 115 may pass from a visible surgical field of view 105 to a hidden surgical field of view 110, and may be adapted to receive the surgical anchor 600. At step 2015, a tissue 315 to be attached to the bone 100 may be retrieved, and one or more sutures 310 may be secured in the tissue 315. An elastomeric membrane 905 may be placed adjacent to the hole 115 in the bone 100 in the hidden surgical field of view 110 at step 2020. At step 2025, a shuttle stitch 205 may be selected. The shuttle stitch 205 may comprise a leading end adapted to pass through the elastomeric membrane 905 and a barb 1005 at the leading end. The barb 1005 may be adapted to resist movement of the shuttle stitch 205 back through the elastomeric membrane 905, thereby capturing the shuttle stitch 205 in the elastomeric membrane 905. The shuttle stitch 205 may be inserted into the elastomeric membrane 905 at step 2030 such that the barb passes into the elastomeric membrane 905 such that the shuttle stitch 205 is captured therein. In various embodiments, the barb 1005 may pass through the elastomeric membrane 905. At step 2035, the elastomeric membrane 905 and the captured shuttle stitch 205 may be moved from the hidden surgical field of view 110 to the visible surgical field of view 105. The shuttle stitch 205 may be removed from the elastomeric membrane 905 at step 2040. The shuttle stitch 205 may be coupled to one or more of the sutures 310. At step 2045, the shuttle stitch 205 and the one or more coupled sutures 310 may be withdrawn back through the hole 115 in the bone 100. The shuttle stitch 205 may then be decoupled from the one or more sutures 310. At step 2050, the one or more sutures 310 may be passed through the central bore 635, and out one or both of the first and second side bores 640, 645. At step 2055, the surgical anchor 600 may be inserted into the hole 115 in the bone 100. Excess slack in the one or more sutures 310 may be removed such that the tissue 315 is positioned against the bone 100 at step 2060. At step 2065, the surgical anchor 600 may be secured in the hole 115 in the bone 100 such that the beveled bottom surface 660 of the head 610 contacts the chamfered edge 705 of the hole 115, thereby immobilizing the one or more sutures 310 between the beveled bottom surface 660 and the chamfered edge 705.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc. and are also not intended to be limiting. Like terms refer to like elements throughout the description.

As used herein, the terms "having", "containing", "including", "comprising", and the like are open ended terms that indicate the presence of stated elements or features, but do not preclude additional elements or features. The articles "a", "an" and "the" are intended to include the plural as well as the singular, unless the context clearly indicates otherwise.

While the present technology has been described in connection with a series of preferred embodiments, these descriptions are not intended to limit the scope of the technology to the particular forms set forth herein. It will be further understood that the methods of the technology are not necessarily limited to the discrete steps or the order of the steps described. To the contrary, the present descriptions are intended to cover such alternatives, modifications, and equivalents as may be included within the spirit and scope of the technology as defined by the appended claims and otherwise appreciated by one of ordinary skill in the art.

What is claimed is:

1. A surgical method for attaching tissue to bone, comprising:
  selecting a surgical anchor, the surgical anchor comprising:
    a shaft comprising a side wall, a top end, a terminal end, and a central axis extending from the top end to the terminal end;
    a head positioned at the top end of the shaft, the head comprising a beveled bottom surface oriented at a first angle relative to the central axis of the shaft;
    a central bore extending through at least a portion of the shaft along the central axis;
    a first side bore extending from the shaft side wall to the central bore and angled at a second angle relative to the central axis of the shaft, the first side bore comprising a first opening in the shaft side wall positioned proximate to an intersection of the beveled bottom surface of the head and the shaft side wall;
    a second side bore positioned a radial distance around the shaft from the first side bore, the second side bore extending from the shaft side wall to the central bore and angled at a third angle relative to the central axis of the shaft, and comprising a second opening in the shaft side wall positioned proximate to the intersection of the beveled bottom surface of the head and the shaft side wall;
  drilling a hole through a bone and chamfering an edge of the hole, the hole passing from a visible surgical field of view to a hidden surgical field of view and adapted to receive the surgical anchor;
  retrieving a tissue to be attached to the bone and securing one or more sutures in the tissue;
  placing an elastomeric membrane adjacent to the hole in the hidden surgical field of view;
  selecting a shuttle stitch comprising a leading end adapted to pass through the elastomeric membrane and a barb at the leading end, the barb adapted to resist movement of the shuttle stitch back through the elastomeric membrane and thereby capturing the shuttle stitch in the elastomeric membrane;
  inserting the shuttle stitch into the elastomeric membrane such that the barb passes into the elastomeric membrane and is captured therein;

moving the elastomeric membrane and the captured shuttle stitch from the hidden surgical field of view to the visible surgical field of view;

removing the shuttle stitch from the elastomeric membrane and coupling the shuttle stitch to the one or more sutures;

withdrawing the shuttle stitch and the coupled one or more sutures back through the hole in the bone and decoupling the shuttle stitch from the one or more sutures;

passing the one or more sutures through the central bore of the surgical anchor and out one or both of the first and second side bores;

inserting the surgical anchor into the hole in the bone;

removing excess slack in the one or more sutures such that the tissue is positioned in contact with the bone; and securing the surgical anchor into the hole in the bone such that the beveled bottom surface of the head contacts the chamfered edge of the hole, thereby immobilizing the one or more sutures between the beveled bottom surface and the chamfered edge.

2. The method of claim 1, wherein drilling the hole through the bone comprises drilling the hole with a diameter less than a diameter of the shaft of the surgical anchor.

3. The method of claim 1, further comprising passing at least one suture out of the first side bore and passing at least one other suture out of the second side bore.

4. The method of claim 1, wherein securing the surgical anchor into the hole comprises rotating the surgical anchor such that threads on the side wall of the shaft engage a side wall of the hole.

5. The method of claim 1, wherein the retrieving a tissue comprises retrieving a tendon.

6. The method of claim 1, wherein the retrieving a tissue comprises retrieving a ligament.

7. The method of claim 1, wherein the placing an elastomeric membrane adjacent to the hole comprises placing a membrane comprising a saturated rubber, an unsaturated rubber, a thermoplastic elastomer, resilin, elastin, polysulfide rubber, elastolefin, or mixtures thereof adjacent to the hole.

8. The method of claim 1, wherein removing the shuttle stitch from the elastomeric membrane comprises removing the barb from the shuttle stitch and pulling the shuttle stitch out of the elastomeric membrane.

* * * * *